(12) United States Patent
Shao et al.

(10) Patent No.: US 9,891,179 B2
(45) Date of Patent: Feb. 13, 2018

(54) APPARATUS AND METHOD FOR PROCESSING AND INTERPRETING NMR LOGGING DATA

(71) Applicant: HALLIBURTON ENERGY SERVICES, INC., Houston, TX (US)

(72) Inventors: Wei Shao, Conroe, TX (US); Songhua Chen, Katy, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/313,893

(22) PCT Filed: Jun. 30, 2016

(86) PCT No.: PCT/US2016/040477
§ 371 (c)(1),
(2) Date: Nov. 23, 2016

(87) PCT Pub. No.: WO2017/023459
PCT Pub. Date: Feb. 9, 2017

(65) Prior Publication Data
US 2017/0176361 A1 Jun. 22, 2017

Related U.S. Application Data

(60) Provisional application No. 62/199,871, filed on Jul. 31, 2015.

(51) Int. Cl.
*G01N 24/08* (2006.01)
*G01R 33/44* (2006.01)
*G01V 3/32* (2006.01)
*E21B 49/00* (2006.01)
*E21B 49/02* (2006.01)
(Continued)

(52) U.S. Cl.
CPC ......... *G01N 24/081* (2013.01); *E21B 49/003* (2013.01); *E21B 49/02* (2013.01); *G01R 33/448* (2013.01); *G01V 3/32* (2013.01); *E21B 47/024* (2013.01); *E21B 47/18* (2013.01)

(58) Field of Classification Search
CPC .... G01N 24/081; G01R 33/448; E21B 47/18; E21B 47/024; E21B 49/003; E21B 49/02
See application file for complete search history.

(56) References Cited

U.S. PATENT DOCUMENTS 6,894,493 B2 5/2005 Hurlimann et al.
6,937,014 B2 * 8/2005 Sun ..................... G01N 24/081
324/300
(Continued)

OTHER PUBLICATIONS

Journal of Applied Geophysics, vol. 103, Apr. 2014, pp. 12-30.
International Search Report and Written Opinion; PCT Application No. PCT/US2016/040477; dated Sep. 12, 2016.

*Primary Examiner* — Dixomara Vargas
(74) *Attorney, Agent, or Firm* — Polsinelli PC

(57) ABSTRACT

Apparatus, method and system for processing and interpreting nuclear magnetic resonance (NMR) data acquired for a formation from within a subterranean wellbore that includes independently obtaining $D-T_1$ and $D-T_2$ from the same set of NMR data using a dual step independent 2D inversion method that provides adequate resolution in all dimensions for $T_1$, $T_2$, and D distributions.

20 Claims, 7 Drawing Sheets

(51) Int. Cl.
*E21B 47/18* (2012.01)
*E21B 47/024* (2006.01)

(56) References Cited

U.S. PATENT DOCUMENTS

| | | | | |
|---|---|---|---|---|
| 6,960,913 | B2* | 11/2005 | Heaton | G01N 24/081 |
| | | | | 324/303 |
| 7,034,528 | B2* | 4/2006 | Minh | G01N 24/081 |
| | | | | 324/303 |
| 7,298,142 | B2 | 11/2007 | Hursan et al. | |
| 7,388,374 | B2* | 6/2008 | Minh | G01N 24/081 |
| | | | | 324/303 |
| 7,500,388 | B2* | 3/2009 | Fujisawa | E21B 49/06 |
| | | | | 73/152.11 |
| 7,538,547 | B2* | 5/2009 | Heaton | G01V 3/32 |
| | | | | 324/303 |
| 7,893,692 | B2* | 2/2011 | Minh | G01V 3/32 |
| | | | | 324/300 |
| 7,924,001 | B2* | 4/2011 | Cao Minh | G01N 24/081 |
| | | | | 324/303 |
| 8,532,929 | B2* | 9/2013 | Li | G01V 3/32 |
| | | | | 324/303 |
| 8,860,413 | B2* | 10/2014 | Hopper | G01R 33/3808 |
| | | | | 324/303 |
| 9,018,950 | B2* | 4/2015 | Li | G01N 24/081 |
| | | | | 324/309 |
| 9,097,818 | B2* | 8/2015 | Hursan | G01V 3/32 |
| 9,222,902 | B2* | 12/2015 | Gruber | G01R 33/448 |
| 9,405,037 | B2* | 8/2016 | Al-Muthana | G01V 3/38 |
| 9,541,513 | B2* | 1/2017 | Paulsen | G01N 24/081 |
| 9,575,203 | B2* | 2/2017 | Chen | G01V 3/32 |
| 9,599,688 | B2* | 3/2017 | Grunewald | G01V 3/14 |
| 9,625,601 | B2* | 4/2017 | Liu | G01V 3/14 |
| 9,703,003 | B2* | 7/2017 | Bennett | G01V 3/32 |
| 9,720,124 | B2* | 8/2017 | Kadayam Viswanathan | G01V 3/14 |
| 9,720,128 | B2* | 8/2017 | Kadayam Viswanathan | G01V 3/32 |
| 9,753,176 | B2* | 9/2017 | Datey | G01V 3/32 |
| 2002/0067164 | A1 | 6/2002 | Venkataramanan et al. | |
| 2003/0128032 | A1 | 7/2003 | Heaton et al. | |
| 2005/0270023 | A1 | 12/2005 | Freedman | |
| 2009/0128144 | A1 | 5/2009 | Freedman et al. | |
| 2010/0277167 | A1 | 11/2010 | Romero | |

* cited by examiner

APPARATUS AND METHOD FOR PROCESSING AND INTERPRETING NMR LOGGING DATA

CROSS-REFERENCE TO RELATED APPLICATIONS

This application is a national stage entry of PCT/US2016/040477 filed Jun. 30, 2016, which claims priority to provisional application No. 62/199,871 filed Jul. 31, 2015, said application is expressly incorporated herein in its entirety.

FIELD

The present disclosure relates to evaluating the fluid productivity of subsurface rock formations. In particular, the present disclosure relates to an apparatus, method, and system for processing and interpreting nuclear magnetic resonance (NMR) data acquired for a formation from within a subterranean wellbore.

BACKGROUND

Wellbores are drilled into the earth for a variety of purposes including tapping into hydrocarbon bearing formations to extract the hydrocarbons for use as fuel, lubricants, chemical production, and other purposes. In order to facilitate characterization of a subterranean formation and the fluids contained therein, it is often desirable to lower a NMR logging tool into a wellbore.

Modern NMR well logging instruments and core analysis instruments are capable of acquiring a large amount of data with different acquisition parameters and pulse sequences. The raw data recorded by NMR logging tools are a series of spin-echo amplitudes (echo trains) as a function of time, usually at fixed or predetermined time increments (bins). The evolution of NMR signal amplitudes acquired with these variations of parameters and pulse sequences is often described in terms of NMR characteristic parameters, such as spin-lattice relaxation time ($T_1$), spin-spin relaxation time ($T_2$), and molecular diffusion (D). These NMR characteristic parameters ($T_1$, $T_2$, and D) can be related to reservoir rock properties, fluid phase saturations and distributions, and hydrocarbon storage and producibility information.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1A:
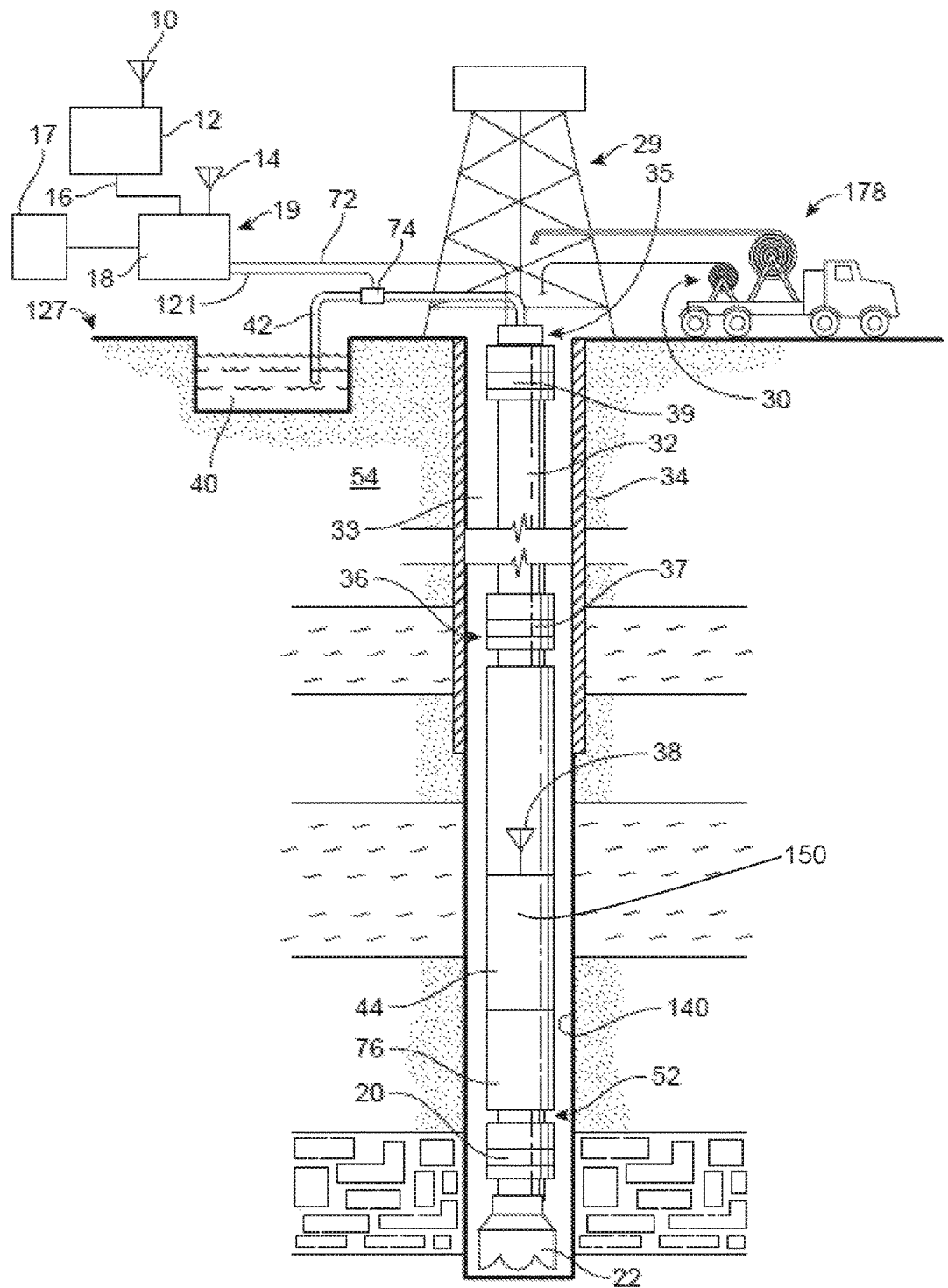
FIG. 1A is a schematic diagram of an embodiment of a wellbore operating environment in which the nuclear magnetic resonance (NMR) apparatus, method, and system may be deployed, according to an exemplary embodiment.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

It should be understood at the outset that although illustrative implementations of one or more embodiments are illustrated below, the disclosed apparatus, methods, and systems may be implemented using any number of techniques. The disclosure should in no way be limited to the illustrative implementations, drawings, and techniques illustrated herein, but may be modified within the scope of the appended claims along with their full scope of equivalents.

Unless otherwise specified, any use of any form of the term "couple," or any other term describing an interaction between elements is not meant to limit the interaction to direct interaction between the elements and also may include indirect interaction between the elements described. In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of this disclosure upon reading the following detailed description, and by referring to the accompanying drawings.

The present disclosure provides an apparatus, method, and system for independently deriving D-$T_1$ and D-$T_2$ maps from the same set of NMR data, without requiring a full 3D inversion of $T_1$, $T_2$, and D. The capability of independently inverting D-$T_1$ and D-$T_2$, as disclosed herein, provides for more accurate fluid-typing in certain cases.

The distributions of NMR characteristic parameters ($T_1$, $T_2$, and D) can be related to reservoir rock properties, fluid phase saturations and distributions, and hydrocarbon storage and producibility information. In order to derive the distributions of $T_1$, $T_2$, and D, or a subset of these, from time-domain NMR measurements, an inversion can be applied to multiple echo trains. When the distributions of all three parameters are derived, the inversion algorithm may be referred to as a 3D inversion. In the most general form of 3D inversion of multiple echo trains, the echo decay functions are expressed in terms of intrinsic spin-spin relaxation time ($T_2$):

$$F_1(t, T_2) = \exp(-t/T_2), \qquad (1)$$

longitudinal relaxation time ($T_1$):

$$F_2(t_W, T_1) = 1 - \exp(-t_W/T_1), \qquad (2)$$

and the additional echo decay due to spin dephasing due to diffusion in a gradient field:

$$F_3(t, t_E, D, G) = \exp(-\gamma^2 G^2 t_E^2 Dt/12), \qquad (3)$$

where $t = it_{E_j}$ is the $i^{th}$ echo in an echo train acquired with the $j^{th}$ interecho time $t_{E_j}$ and the $k^{th}$ wait time $t_{W_k}$ and the echo signals are contributed from $l^{th}$ sensitive volume in which the field gradient strength the spins experience is $G_l$. The relaxation times and diffusivity of the proton system are influenced by the fluid types, the viscosity of the fluid, the interaction between the fluid molecules and the molecules in the rock matrix. Therefore, $T_1$, $T_2$, and D are expected to have distributions of values. The 3D inversion of multiple echo trains can be used to obtain the distributions of $T_1$, $T_2$, and D. Individual echoes in any of the multiple echo trains can be described by:

$$E(i,j,k) = \sum_{m=1}^{M} \sum_{n=1}^{N} \sum_{p=1}^{P} E_{0,mnp}[1-\exp(-t_{W_k}/T_{1,n})] \exp(-i \cdot t_E/T_{2,n}) \exp(-\gamma^2 G_l^2 \cdot t_{E_j}^2 D_p/12) + \text{noise} \qquad (4)$$

The solution $E_{0,mnp}$ can be obtained by solving the linear equation sets in the form of Eqn. 4, plus often the non-negative constraint of $$E_{0,mnp} \geq 0 \qquad (5)$$

is imposed. To simplify the notations, Eqn. 4 and the constraint of Eqn. 5 may be written in matrix form:

$$AX = b, X \geq 0. \qquad (6)$$

However, directly solving the non-negative $E_{0,mnp}$ is time-consuming and computationally expensive. Additionally, the large number of unknowns (M×N×P) may exceed the number of echoes, resulting in an under-determined problem. The linear system can be solved by the least squares method which involves the matrix multiplication of A'×A and its inverse. The computational complexity of the matrix multiplication and its inverse is 0(M×N×P). For a 3D inversion with a size of $20T_2 \times 20D \times 20T_1$, the resolution of $T_2$ and $T_1$ may not be good enough for petrophysical interpretation. Assuming that the number of acquired echoes is 4000, almost 16 seconds is required for the matrix multiplication A'×A in a Matlab platform. Therefore 3D NMR inversion is normally too time consuming to be used for field data interpretation, especially because the computation has to be performed at each depth level in the wellbore and on the order of 4-8 samples/foot.

In order to improve the computational efficiency of determining the distributions of $T_1$, $T_2$, and D, a valid physical constraint can be applied based on the intrinsic $T_2$ and $T_1$ relationship of fluids in porous media. In general, bulk $T_1$ and intrinsic $T_2$ of liquid water and light or medium viscose oils and hydrocarbon gases are substantially close to unity. However, when affected by the pore surface, the $T_1/T_2$ ratio may increase somewhat, generally in the range of 1 to 5. On the other hand, heavy oil and tar are expected to have a higher $T_1/T_2$ ratio for the range that is generally observable by NMR logging instruments. Therefore it is generally true that:

$$1 \leq (R = T_1/T_2) \leq 10. \qquad (7)$$

When the physical constraint of Eqn. 7 is applied, Eqn. 4 is rewritten as a modified 3D inversion model, often termed a "2.5D model"

$$E(i,j,k) = \sum_{m=1}^{M'} \sum_{n=1}^{N} \sum_{p=1}^{P} E_{0,mnp}[1-\exp(-t_{W_k}/R_m T_{2,n})] \exp(-i \cdot t_E/T_{2,n}) \exp(-\gamma^2 G_l^2 \cdot t_{E_j}^3 D_p/12), \qquad (8)$$

where M' is often a much smaller number than M, thereby significantly reducing the size of the matrix. The solution of the inversion of Eqn. 8 with Eqn. 5 is M' number of D-$T_2$ maps, each with a distinctive R. A single combined D-$T_2$ map may be computed by co-adding, pixel-by-pixel, the intensity of the individual D-$T_2$ maps:

$$\sum_{m=1}^{M'} E_{0,mnp} = E_{0,np}, \qquad (9)$$

For petrophysical interpretation purposes, it is preferred to obtain the D-$T_1$ map in addition to the D-$T_2$ map. The D-$T_1$ map may be obtained by applying the $R_m$ to the parallel shift of the intensities of $E_{0,mnp}$ to $E_{0,mn'p}$, where the $n'^{th}$ pixel $T_1$ value equals or substantially equals $T_{1,n'} = T_{2,n} \cdot R_m$. Then the m D-$T_1$ maps can be either stacked or the logarithmic mean of $R_m$'s corresponding to different m's can be computed for individual D-$T_2$ pixels, then the D-$T_2$ intensities of the n-$p^{th}$ pixel is shifted by the factor of $R_{LM,np}$. However, this method cannot adequately distinguish a case where two fluids do not have observable contrast by D and $T_2$, but have sufficient $T_1$ contrast, since the reconstructed D-$T_1$ map is not independent of the D-$T_2$ map. Therefore, it is desirable to independently determine D-$T_1$ and D-$T_2$ maps from the same set of acquired NMR data.

The present disclosure provides an apparatus, method, and system for independently deriving D-$T_1$ and D-$T_2$ maps from the same set of NMR data, without requiring a full 3D inversion of $T_1$, $T_2$, and D. According to the present disclosure, D-$T_1$ maps can be obtained from acquired NMR data by performing a second inversion:

$$E(i,j,k) = \sum_{m=1}^{M''} \sum_{n=1}^{N} \sum_{p=1}^{P} E_{0,mnp}[1-\exp(-t_{W_k}/T_{1,n})] \exp(-i \cdot t_E R_m/T_{1,n}) \exp(-\gamma^2 G_l^2 \cdot t_{E_j}^3 D_p/12), \qquad (10)$$

where M'' is a smaller number than M, and can be the same or different than M'. Performance of the second inversion is computationally efficient due to the significant reduction in the size of the matrix necessary for computation. The solution of the inversion of Eqn. 10 with the constraint of Eqn. 5 is M'' number of D-$T_1$ maps, each with a distinctive R. A single combined D-$T_1$ map may be computed by co-adding, pixel-by-pixel, the intensity of the individual D-$T_1$ maps:

$$\sum_{m=1}^{M''} E_{0,mnp} = E_{0,np}. \qquad (11)$$

The dual step independent inversion of D-$T_1$ and D-$T_2$ provides adequate resolution in all dimensions for $T_1$, $T_2$, and D distributions. The nuclear magnetic resonance (NMR) apparatus, method, and system, disclosed herein, provide accurate $T_1$ and D-$T_1$ information about the fluid and reservoir rock as a result of performing two independent inversions of acquired NMR data to yield separate D-$T_1$ and D-$T_2$ results. Additionally, the combination of the independently derived D-$T_1$ and D-$T_2$ results provided by the apparatus, method, and system, disclosed herein, can be used to deliver improved fluid-typing information. For instance, the combination of independently derived D-$T_1$ and D-$T_2$ results, can be used to identify certain fluids, such as heavy oil, that cannot be identified by D-$T_2$ or D-$T_1$ alone. The apparatus, method, and system disclosed herein further provides for independently-derived D-$T_1$ and D-$T_2$ with improved fidelity of the $T_1$ spectrum.

FIG. 1A illustrates a wellbore operating environment in which the nuclear magnetic resonance (NMR) apparatus, method, and system may be deployed, according to an exemplary embodiment of the present disclosure. As shown in FIG. 1A, NMR logging can be conducted during drilling operations in a subterranean well environment. A wellbore 140 is shown that has been drilled into the earth 54 from the ground's surface 127 using a drill bit 22. The drill bit 22 is located at the bottom, distal end of the drill string 32 and the bit 22 and drill string 32 are being advanced into the earth 54 by the drilling rig 29. The drilling rig 29 can be supported directly on land as shown or on an intermediate platform if at sea. For illustrative purposes, the top portion of the wellbore includes casing 34 that is typically at least partially made up of cement and which defines and stabilizes the wellbore after being drilled. The drill bit 22 can be rotated via rotating the drill string, and/or a downhole motor near the drill bit 22.

As shown in FIG. 1A, the drill string 32 supports several components along its length, including a nuclear magnetic resonance (NMR) data acquisition tool 150. A sensor sub-unit 52 is shown for detecting conditions near the drill bit 22, conditions which can include such properties as formation fluid density, temperature and pressure, and azimuthal orientation of the drill bit 22 or string 32. Measurement while drilling (MWD)/logging while drilling (LWD) procedures are supported both structurally and communicatively, which can include the NMR logging operations as discussed herein. The instance of directional drilling is illustrated in FIG. 1A. The lower end portion of the drill string 32 can include a drill collar proximate to the drilling bit 22 and a drilling device such as a rotary steerable drilling device 20, or other drilling devices disclosed herein. The drill bit 22 may take the form of a roller cone bit or fixed cutter bit or any other type of bit known in the art. The sensor sub-unit 52 is located in or proximate to the rotary steerable drilling device 20 and advantageously detects the azimuthal orientation of the rotary steerable drilling device 20. Other sensor sub-units 35, 36 are shown within the cased portion of the well which can be enabled to sense nearby characteristics and conditions of the drill string, formation fluid, casing and surrounding formation. Regardless of which conditions or characteristics are sensed, data indicative of those conditions and characteristics is either recorded downhole, for instance at the processor 44 for later download, or communicated to the surface either by wire using repeaters 37, 39 up to surface wire 72, or wirelessly or otherwise. If wirelessly, the downhole transceiver (antenna) 38 can be utilized to send data to a local processor 18, via topside transceiver (antenna) 14. There the data may be either processed or further transmitted along to a remote processor 12 via wire 16 or wirelessly via antennae 14 and 10.

Figure 1B:
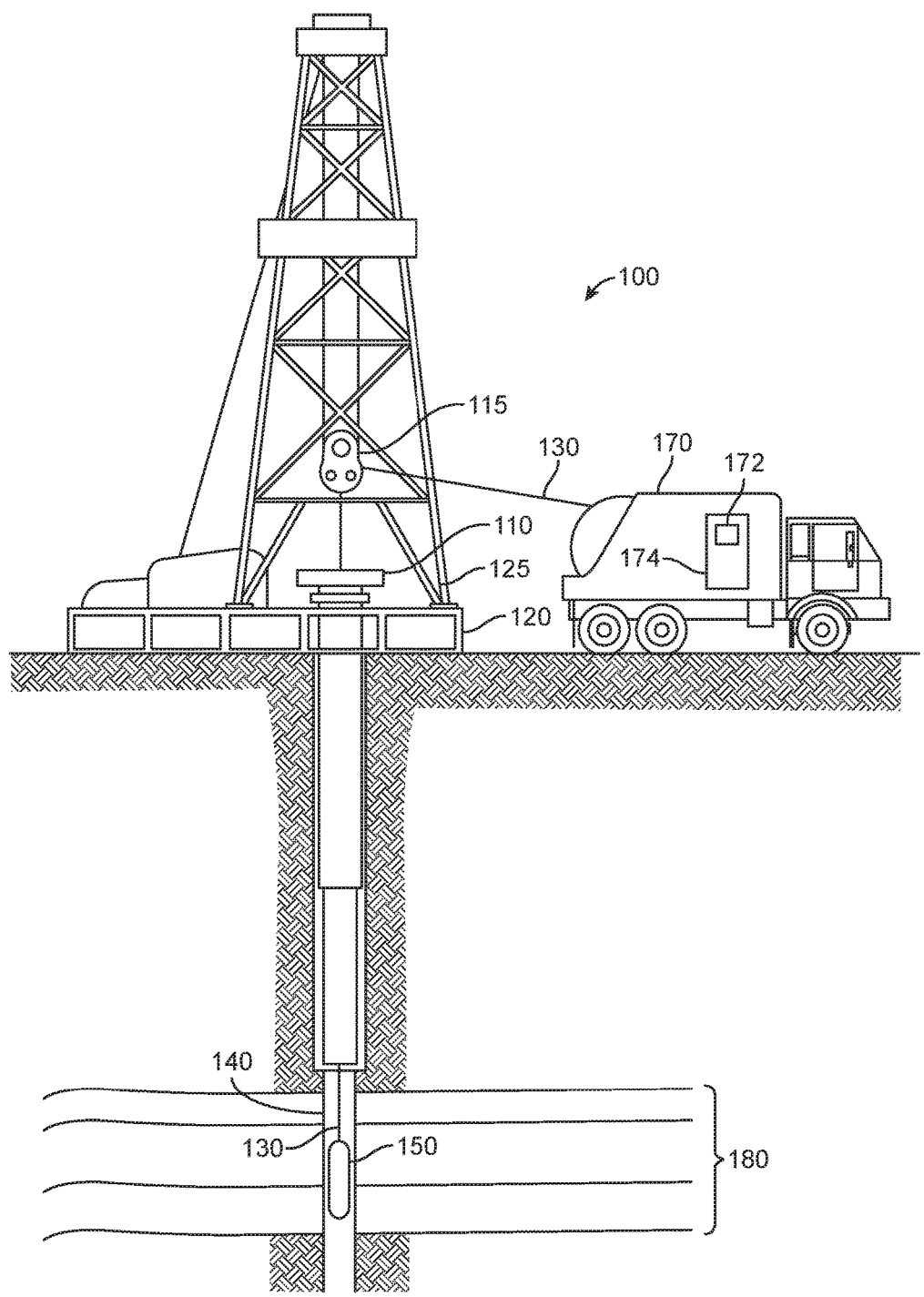
FIG. 1B is a schematic diagram of an embodiment of a wellbore operating environment in which the nuclear magnetic resonance (NMR) apparatus, method, and system may be deployed, according to an exemplary embodiment.

Coiled tubing 178 and wireline 30 can additionally be deployed as an independent service upon removal of the drill string 32, as shown for example in FIG. 1B. The possibility of an additional mode of communication is contemplated using drilling mud 40 that is pumped via conduit 42 to a downhole mud motor 76. The drilling mud is circulated down through the drill string 32 and up the annulus 33 around the drill string 32 to cool the drill bit 22 and remove cuttings from the wellbore 140. For purposes of communication, resistance to the incoming flow of mud can be modulated downhole to send backpressure pulses up to the surface for detection at sensor 74, and from which representative data is sent along communication channel 121 (wired or wirelessly) to one or more processors 18, 12 for recordation and/or processing.

The sensor sub-unit 52 is located along the drill string 32 above the drill bit 22. The sensor sub-unit 36 is shown in FIG. 1A positioned above the mud motor 76 that rotates the drill bit 22. Additional sensor sub-units 35, 36 can be included as desired in the drill string 32. The sub-unit 52 positioned below the motor 76 communicates with the sub-unit 36 in order to relay information to the surface 127.

A surface installation 19 is shown that sends and receives data to and from the well. The surface installation 19 can exemplarily include a local processor 18 that can optionally communicate with one or more remote processors 12, 17 by wire 16 or wirelessly using transceivers 10, 14.

The exemplary rotary steerable drilling device 20 schematically shown in FIG. 1A can also be referred to as a drilling direction control device or system. As shown, the rotary drilling device 20 is positioned on the drill string 32 with drill bit 22. However, one of skill in the art will recognize that the positioning of the rotary steerable drilling device 20 on the drill string 32 and relative to other components on the drill string 32 may be modified while remaining within the scope of the present disclosure.

FIG. 1B illustrates a wellbore operating environment in which the nuclear magnetic resonance (NMR) apparatus, method, and system may be deployed, according to an exemplary embodiment of the present disclosure. As depicted, the operating environment 100 includes a drilling platform 120 equipped with a derrick 125 that supports a hoist 115. Drilling oil and gas wells is commonly carried out using a string of drill pipes connected together so as to form a drilling string that is lowered through a rotary table 110 into a wellbore or borehole 140.

Here it is assumed that the drill string has been temporarily removed from the wellbore 140 to allow a nuclear magnetic resonance (NMR) data acquisition tool 150 to be lowered into the wellbore 140. The NMR data acquisition tool may be conveyed in the wellbore 140 by any conveyance 130 including, but not limited to, wireline, logging cable, slickline, tubing, pipe, metallic wire, non-metallic wire, or composite wire. Typically, the NMR data acquisition tool 150 is lowered to the bottom of the region of interest and subsequently pulled upward at a substantially constant speed. During the upward trip, one or more NMR sensors in the NMR data acquisition tool 150 may be used to perform measurements on the subsurface formations 180 adjacent to the wellbore 140 as they pass by.

The measurement data, including NMR echo train data for a plurality of echo trains, can be communicated to a logging facility 170 for storage, processing, and analysis. The logging facility 170 may be provided with electronic equipment for various types of signal processing. For example, the logging facility 170 may include one or more NMR data processing units 174 for the processing of NMR data. In some instances, the NMR data processing unit 174 may be similar to or identical to the NMR data processing unit 234 described with respect to FIG. 2. In some cases, the NMR data processing unit 174 can be communicatively coupled to one or more displays 172.

In some cases, the NMR data acquisition tool 150 can be housed in a downhole tool body comprising additional downhole logging tools. In some cases, the logging facility 170 may store, process, and/or analyze logging data from more than one downhole logging tools.

Although FIGS. 1A and 1B depict a vertical wellbore 140, the present disclosure is equally well-suited for use in wellbores having other orientations including horizontal wellbores, slanted wellbores, multilateral wellbores or the like. Also, even though FIGS. 1A and 1B depict an onshore operation, the present disclosure is equally well-suited for use in offshore operations.

Although FIG. 1B shows an exemplary environment relating to NMR logging in the absence or temporary cessation of drilling operations, the present disclosure is equally well-suited for use in "logging while drilling" (LWD) operations, for example, as shown in FIG. 1A. As such, the present disclosure is equally well-suited for use in operations where the drilling assembly includes the NMR data acquisition tool thereby providing for NMR data acquisition during drilling operations, when measurements may be less affected by fluid invasion. Additionally, the present disclosure is equally well-suited to the characterization of core samples brought to the surface from subterranean formations. As such, the present disclosure is equally well-suited in the use of core analysis equipment for the characterization of core samples in a laboratory or surface environment.

Figure 2:
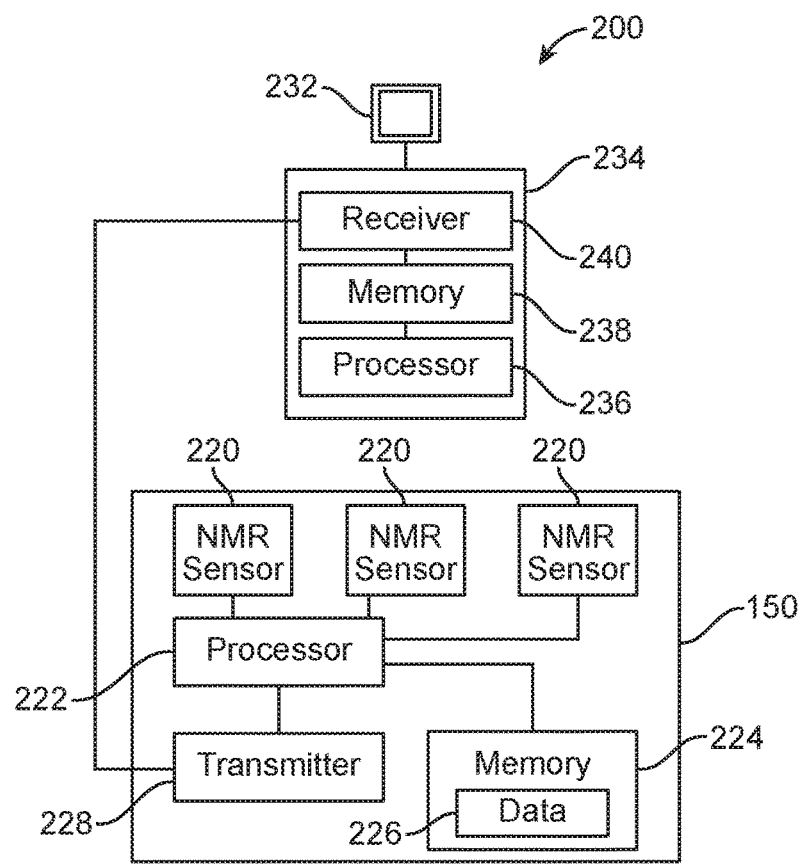
FIG. 2 illustrates an NMR apparatus, according to an exemplary embodiment.

A variety of apparatus, systems and methods may be used to implement the dual step independent inversion method disclosed herein. For instance, FIG. 2 illustrates an NMR apparatus 200, according to an exemplary embodiment of the present disclosure. As shown in FIG. 2, the NMR apparatus 200 may include a NMR data acquisition tool 150 communicatively coupled to a NMR data processing unit 234. The NMR data acquisition tool 150 may include one or more NMR sensors 220 communicatively coupled to a NMR data acquisition processor 222. The NMR data acquisition tool 150 may further include data acquisition memory 224 capable of storing instructions that when executed by the data acquisition processor 222 causes the data acquisition processor 222 to acquire NMR data in a time domain from a subterranean formation, or core sample therefrom, using one or more NMR sensors 220. The data acquisition memory 224 is also capable of storing acquired NMR data 226.

The NMR data acquisition processor 222 may optionally be communicatively coupled to a transmitter 228 capable of transmitting the acquired NMR data 226 to the NMR data processing unit 234.

The NMR data processing unit 234 can include a data processor 236 communicatively coupled to data processing memory 238 capable of storing instructions that when executed by the data processor 236 causes the data processor 236 to receive the NMR data 226 from the NMR data acquisition tool 150 and perform a first inversion of the NMR data 226 using a physical constraint in place of $T_1$ to derive $D-T_2$ and perform a second independent inversion of the acquired NMR data 226 using a physical constraint in place of $T_2$ to derive $D-T_1$. The NMR data processing unit 234 may optionally have a receiver 240 capable of receiving NMR data 226 from the transmitter 228 of the NMR data acquisition tool 150. The NMR data processing unit 234 may also optionally have a display 232 capable of displaying the NMR data inversion result. In some cases, the display 232 can display $D-T_1$ or $D-T_2$ intensity maps.

Figure 3:
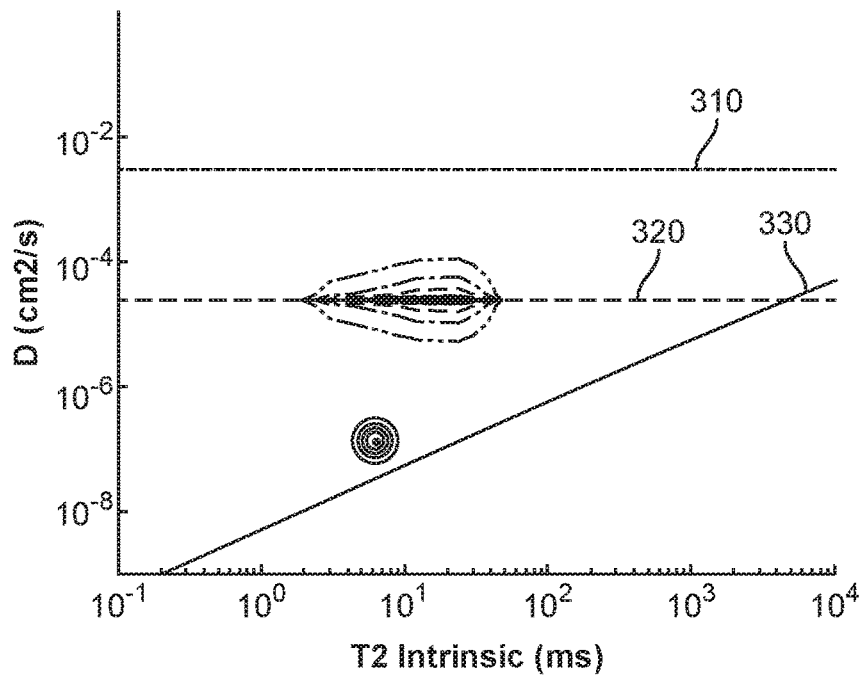
FIG. 3 illustrates a D-$T_2$ map for a simulated formation, according to an exemplary embodiment.

The capability of independently inverting $D-T_1$ and $D-T_2$, as disclosed herein, is important for accurate fluid-typing in certain cases. The improved $D-T_1$ inversion result, obtained according to the method of the present disclosure, can be shown by way of a comparative example using synthetic echo train data as inputs for the inversion processing. FIG. 3 illustrates a $D-T_2$ map for a simulated formation that contains 40% saturation of a heavy oil of 16 API gravity, with 100 gas-oil ratio (GOR) at 114° F. and 1000 psi, and 60% of water saturation distributed mainly as bulk volume irreducible (BVI), but having the tail part in the clay-bound-water (CBW) and free-fluid index (FFI) ranges. The $T_1/T_2$ ratio was set to be 1.5 for water and 4 for oil. Label 310 depicts the gas diffusivity line while label 320 depicts the water diffusivity line. Label 330 illustrates the oil diffusivity and viscosity line.

Table 1 illustrates a pulse sequence activation set used as inputs in the inversion processing. The activation set was generated to include 9 echo trains with different inter-echo times (TE), wait times (TW), and number of echoes. The activation set also corresponded to different noise levels and field gradient values. Noise-contaminated echo trains based on these data acquisition and tool attributes were generated using a random noise generator. The synthetic echo train data illustrated in Table 1 were used as inputs in the inversion processing to provide the inversion results shown in FIGS. 4-7.

Figure 4:
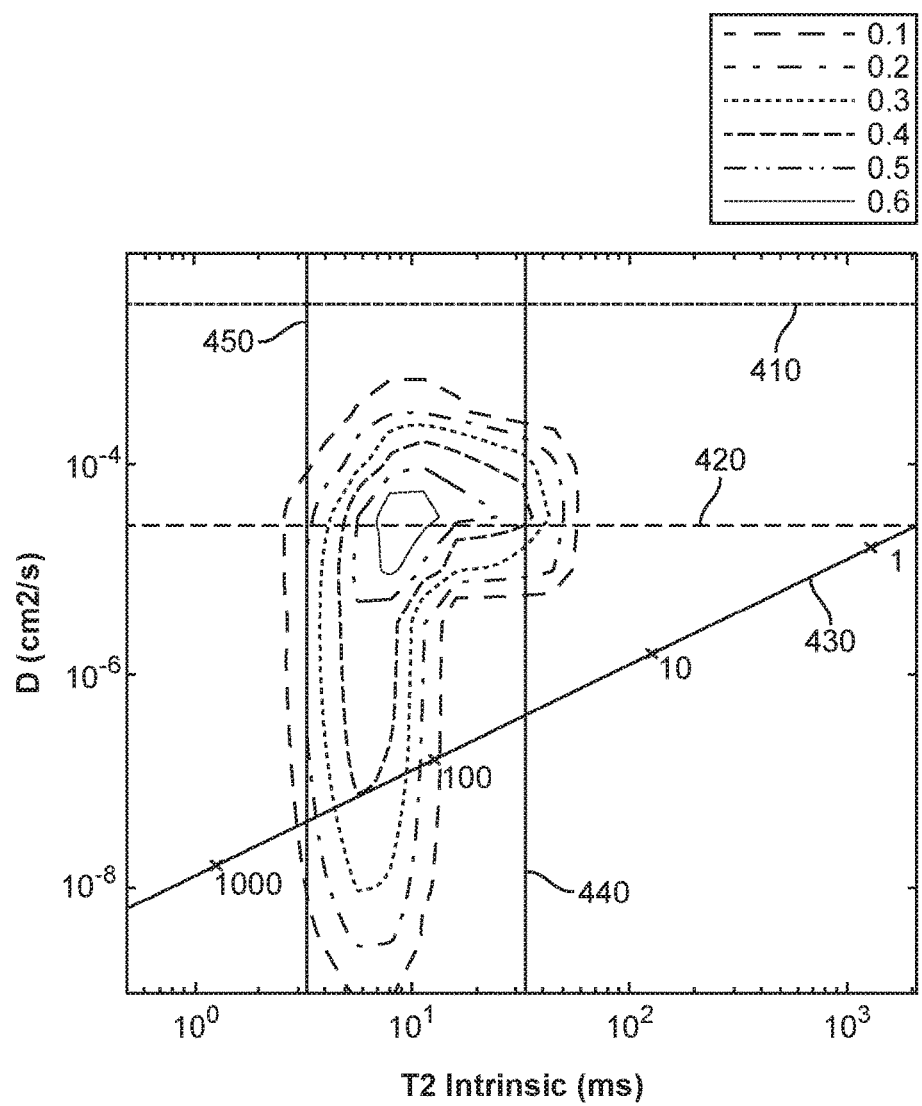
FIG. 4 illustrates a D-$T_2$ intensity map produced from synthetic echo train data by the dual step independent D-$T_2$ inversion method disclosed herein, according to an exemplary embodiment.
Figure 5:
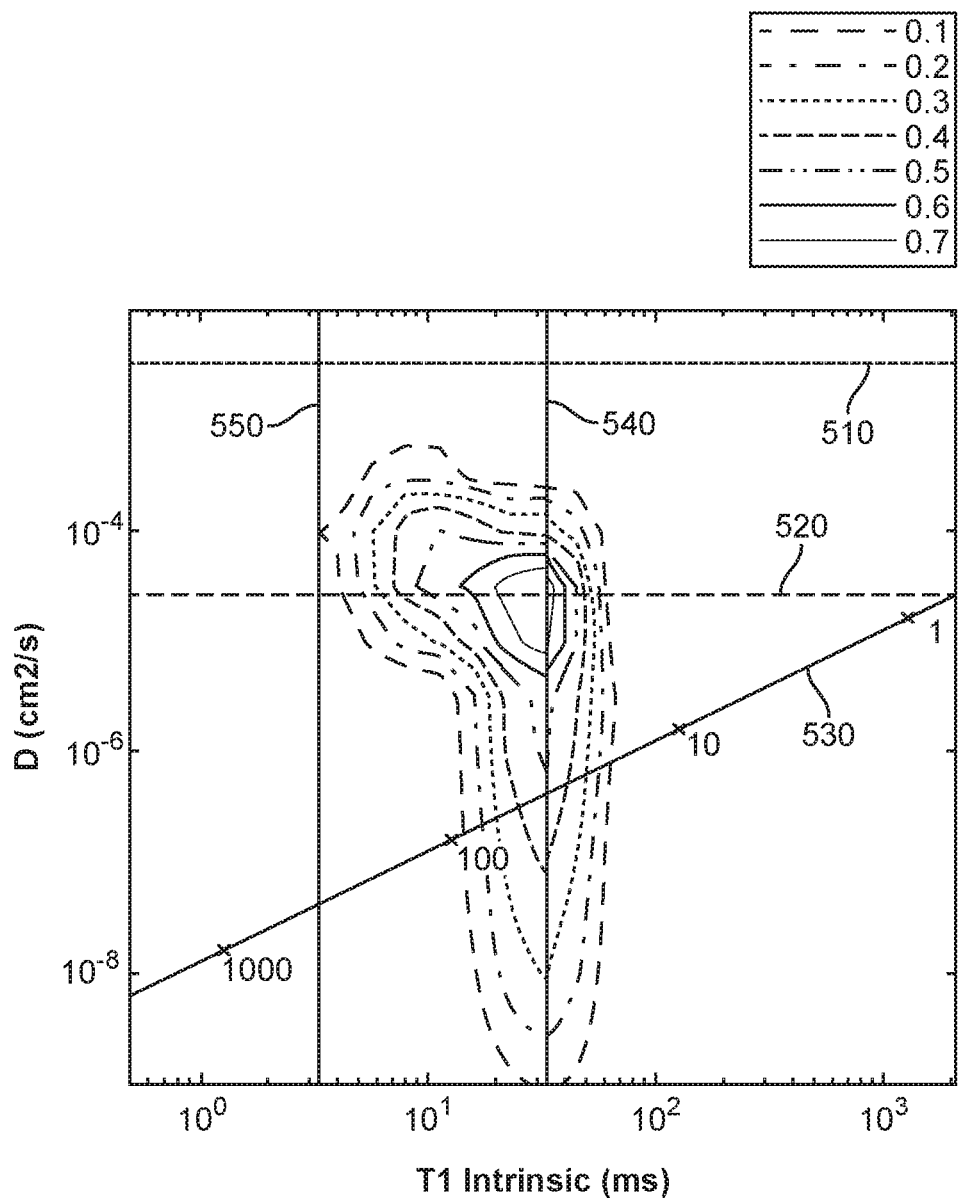
FIG. 5 illustrates a D-$T_1$ intensity map produced from synthetic echo train data by the dual step independent D-$T_1$ inversion method disclosed herein, according to an exemplary embodiment.

FIGS. 4 and 5 illustrate the inversion results generated by inversion of the synthetic echo train data presented in Table 1 using the dual step independent inversion method disclosed herein (e.g., Eqns. 10 and 11). More specifically, FIG. 4 illustrates a $D-T_2$ intensity map and FIG. 5 illustrates a $D-T_1$ intensity map produced by the dual step independent inversion method according to an exemplary embodiment of the present disclosure. In FIG. 4, label 410 depicts the gas diffusivity line while label 420 depicts the water diffusivity line. Label 430 illustrates the oil diffusivity and viscosity line, while labels 440 and 450 represent the $T_2$ cutoff lines. With respect to FIG. 5, label 510 depicts the gas diffusivity line while label 520 depicts the water diffusivity line. Label 530 illustrates the oil diffusivity and viscosity line, while labels 540 and 550 represent the $T_1$ cutoff lines.

TABLE 1

| TW (ms) | TE (ms) | Number of Echoes | Gradient (G/cm) |
|---------|---------|------------------|-----------------|
| 8866    | 0.3     | 2000             | 40              |
| 5       | 0.2     | 50               | 40              |
| 10      | 0.2     | 50               | 40              |
| 8866    | 2.4     | 250              | 30              |
| 8865    | 3.6     | 167              | 35              |
| 8866    | 6       | 100              | 40              |
| 30      | 0.2     | 100              | 40              |
| 100     | 0.2     | 300              | 40              |
| 300     | 0.2     | 500              | 20              |
| 3       | 0.2     | 50               | 40              |

As a result of the fast relaxation of heavy oil, the sensitivity to the diffusivity contrast from the NMR measurements is insufficient to clearly identify the heavy oil from either the $D-T_1$ (FIG. 5) or $D-T_2$ (FIG. 4) intensity maps alone. However, by comparing the two intensity maps shown in FIGS. 4 and 5, the clear shift of the heavy oil signal with respect to water can be readily identified.

Figure 6:
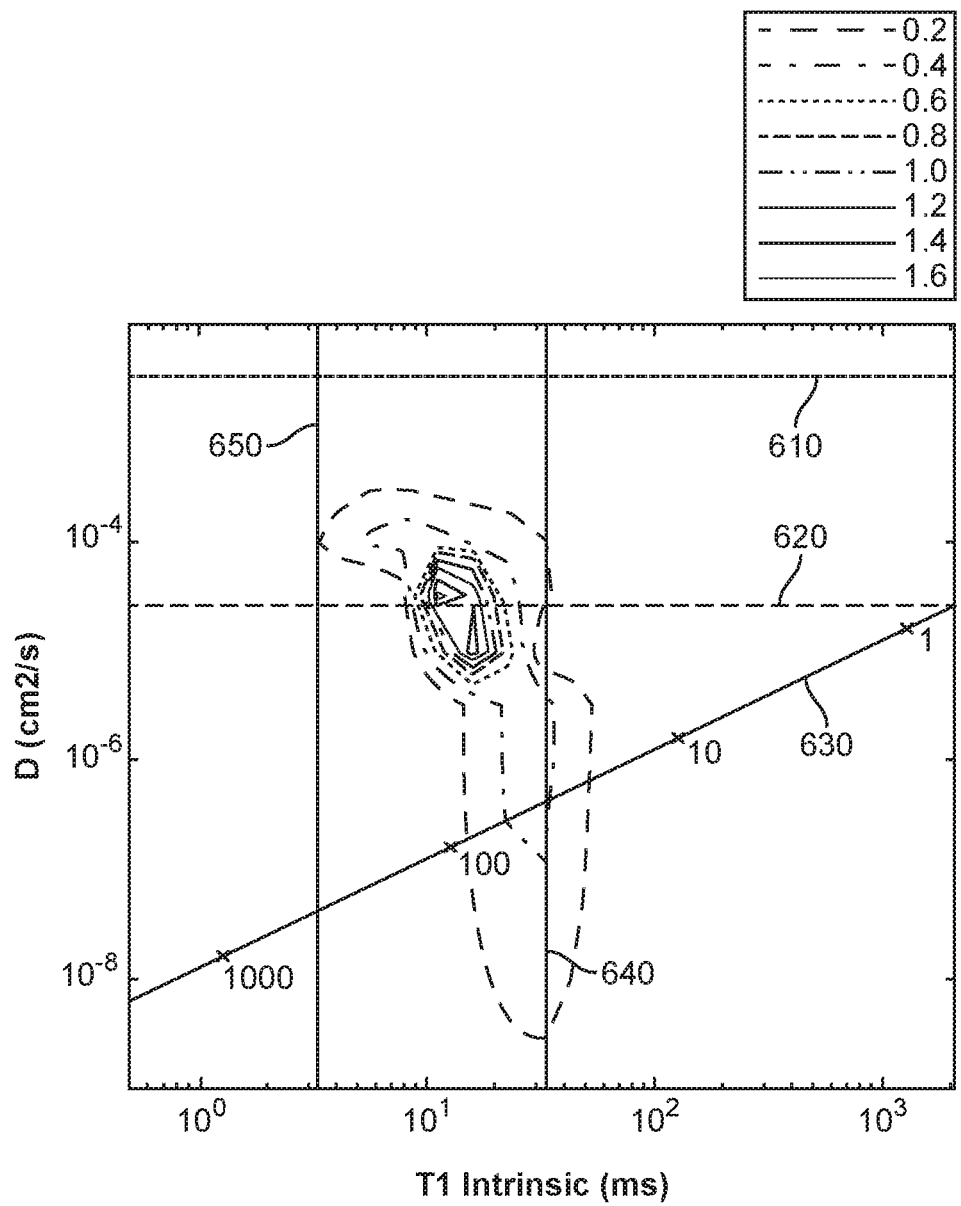
FIG. 6 illustrates a comparative example in the form of a D-$T_1$ intensity map reconstructed from the inversion result illustrated in FIG. 4 from the same synthetic echo train data processed according to the D-$T_2$ inversion method of Eqns. 8 and 9.

FIG. 6 illustrates a comparative example in the form of a $D-T_1$ intensity map reconstructed from the inversion result illustrated in FIG. 4 from the same synthetic echo train data processed according to the $D-T_2$ inversion method of Eqns. 8 and 9. As shown in FIG. 6, the reconstructed $D-T_1$ map has poor resolution as compared to the $D-T_1$ map illustrated in FIG. 5, that was generated according to the dual step independent inversion method disclosed herein (e.g., Eqns. 10 and 11). In FIG. 6, label 610 depicts the gas diffusivity line while label 620 depicts the water diffusivity line. Label 630 illustrates the oil diffusivity and viscosity line, while labels 640 and 650 represent the $T_2$ cutoff lines.

As demonstrated by this comparative example, the reconstructed $D-T_1$ map (FIG. 6) does not have adequate accuracy and resolution in the $T_1$ dimension. In contrast, the $D-T_1$ intensity map resulting from the dual step independent inversion method (FIG. 5) provides adequate resolution in the $T_1$ dimension allowing for more accurate fluid-typing. As shown in this comparative example, the combination of independently obtained D–$T_1$ and D–$T_2$ intensity maps (FIGS. 4 and 5) generated according to the dual step independent inversion method, as described in the present disclosure, can readily identify certain fluids, such as heavy oil, that cannot be identified using the reconstructed D–$T_1$ map derived from the D–$T_2$ inversion.

Figure 7:
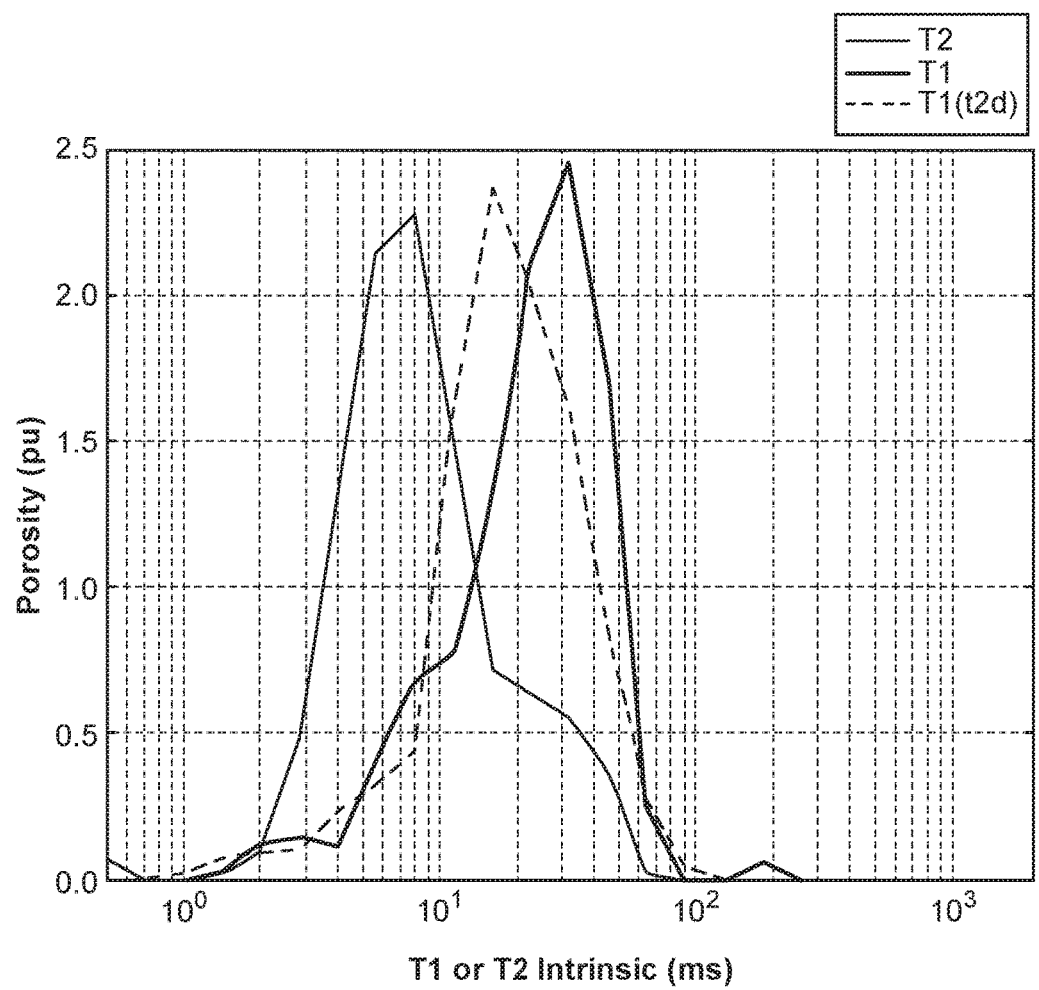
FIG. 7 illustrates $T_1$ and $T_2$ curves derived from D-$T_1$ and D-$T_2$ intensity maps generated according to the dual step independent inversion method disclosed herein and provides comparison to the $T_1$(t2d) curve derived from D-$T_2$ maps obtained using the D-$T_2$ inversion method described in Eqns. 8 and 9.

The advantage of using the independently obtained D–$T_1$ and D–$T_2$ intensity maps, resulting from the dual step independent inversion method (e.g., Eqns. 10 and 11), disclosed herein, is shown by the example illustrated in FIG. 7. The $T_1$ and $T_2$ curves depicted in FIG. 7 were derived from the D–$T_1$ and D–$T_2$ intensity maps generated according to the dual step independent inversion method (e.g., Eqns. 10 and 11) described in the present disclosure. In contrast, the $T_1$(t2d) curve depicted in FIG. 7 was derived from the D–$T_2$ maps using the D–$T_2$ inversion described in Eqns. 8 and 9. As shown in FIG. 7, the $T_1$(t2d) curve derived from D–$T_2$ inversion method according to Eqns. 8 and 9 failed to correctly identify the heavy oil peak shift.

As disclosed herein, a method of evaluating a subsurface formation, or core sample therefrom, by independently deriving D–$T_1$ and D–$T_2$ from the same set of acquired NMR data is provided. The method includes providing a nuclear magnetic resonance (NMR) data acquisition tool. The NMR data acquisition tool can include one or more NMR sensors, a NMR data acquisition processor communicatively coupled to the one or more NMR sensors, and a data acquisition memory communicatively coupled to the NMR data acquisition processor. The data acquisition memory can store instructions that when executed by the data acquisition processor causes the data acquisition processor to acquire NMR data in a time domain from a subterranean formation. The method can further include lowering the NMR data acquisition tool to a desired location within a wellbore and acquiring, at the NMR data acquisition tool, NMR data. The NMR data can include NMR data parameters, including spin-lattice relaxation ($T_1$), spin-spin relaxation time ($T_2$), and molecular diffusion (D). Each NMR data parameter can be included in a plurality of bins. The method can further include receiving the acquired NMR data at a NMR data processing unit communicatively coupled to the NMR data acquisition tool. The NMR data processing unit can include a data processor and data processing memory. The method can further include performing, at the data processor, a first inversion of the NMR data using a physical constraint in place of $T_1$ to derive D–$T_2$ and performing, at the data processor, a second independent inversion of the acquired NMR data using a physical constraint in place of $T_2$ to derive D–$T_1$.

The physical constraint included in the method can include a finite range of $T_1/T_2$ values for fluids in the bulk state or in rocks. The finite range of $T_1/T_2$ values can be between about 1 and 10. The first inversion may include a full parameter range of $T_2$, a full parameter range of D, and a full parameter range of $T_1/T_2$, where the full parameter range of $T_1/T_2$ comprises fewer bins than the number of $T_2$ bins and D bins. The full parameter range of $T_1/T_2$ can be between about 1 and 10, the full parameter range of $T_2$ can be between about 0.5 seconds and 5 seconds, and the full parameter range of D can be between about $10^{-9}$ cm$^2$/s and $10^{-2}$ cm$^2$/s. The first inversion can be carried out by using Eqns. 5 and 8, where R=$T_1/T_2$.

The method can further include comprising displaying, at the NMR data processing unit, the first inversion result as a D–$T_2$ map. The second inversion can include a full parameter range of $T_1$, a full parameter range of D, a full parameter range of $T_1/T_2$, where the full parameter range of $T_1/T_2$ comprises fewer bins than the number of $T_1$ bins and D bins. The full parameter range of $T_1/T_2$ can be between about 1 and 10, the full parameter range of $T_1$ can be between about 0.5 seconds and 5 seconds, and the full parameter range of D can be between about $10^{-9}$ cm$^2$/s and $10^{-2}$ cm$^2$/s. The second inversion can be carried out using Eqns. 5 and 10, where R=$T_1/T_2$.

The method can further include displaying, at the NMR processing unit, the second inversion result as a D–$T_1$ map. The method can further include deriving the $T_1$ distribution and the $T_2$ distribution. The $T_1$ distribution can be derived according to the following equation:

$$\varphi_{T1,i} = \Sigma_{p=1}^{P} E_{0,np}, \quad (12)$$

where: n=1:N $T_1$ bins and p=1:P R bins. The $T_2$ distribution can be derived according to the following equation:

$$\varphi_{T2,i} = \Sigma_{p=1}^{P} E_{0,mp} \quad (13)$$

where: m=1:M $T_2$ bins and p=1:P R bins.

The NMR data included in the method can be multiple echo trains. The NMR data acquisition tool included in the method can be coupled to a drill string or integrated into a bottom-hole assembly near the drill bit. The method can further include storing the NMR data at the data acquisition memory. The method can further include transmitting the NMR data from the NMR data acquisition tool and receiving the NMR data at the NMR data processing unit.

As disclosed herein, a system for evaluating a subsurface formation, or core sample therefrom, by independently deriving D–$T_1$ and D–$T_2$ from the same set of acquired NMR data is provided. The system includes an apparatus that includes a nuclear magnetic resonance (NMR) data acquisition tool and a NMR data processing unit communicatively coupled to the NMR data acquisition tool. The NMR data acquisition tool can include one or more NMR sensors, a NMR data acquisition processor communicatively coupled to the one or more NMR sensors, and data acquisition memory storing instructions that when executed by the data acquisition processor causes the data acquisition processor to acquire NMR data in a time domain from a subterranean formation. The NMR data can include NMR data parameters including spin-lattice relaxation ($T_1$), spin-spin relaxation time ($T_2$), and molecular diffusion (D). Each NMR data parameter can be included in a plurality of bins. The NMR data processing unit can include a data processor and data processing memory. The data processing memory can store instructions that when executed by the data processor causes the data processor to receive the NMR data from the NMR data acquisition, perform a first inversion of the NMR data using a physical constraint in place of $T_1$ to derive D–$T_2$, and perform a second independent inversion of the acquired NMR data using a physical constraint in place of $T_2$ to derive D–$T_1$. The physical constraint may include a finite range of $T_1/T_2$ values for fluids in the bulk state or in rocks. The finite range of $T_1/T_2$ values can be between about 1 and 10. The first inversion can include a full parameter range of $T_2$, a full parameter range of D, and a full parameter range of $T_1/T_2$, where the full parameter range of $T_1/T_2$ includes fewer bins than the number of $T_2$ bins and D bins. The full parameter range of $T_1/T_2$ can be between about 1 and 10, the full parameter range of $T_2$ can be between about 0.5 seconds and 5 seconds, and the full parameter range of D can be between about $10^{-9}$ cm$^2$/s and $10^{-2}$ cm$^2$/s. The first inversion can be carried out using Eqns. 5 and 8, where R=$T_1/T_2$. The system can further include a display communicatively coupled to the NMR data processing unit, where the display is configured to display the first inversion result as a D–$T_2$ map.

The second inversion can include a full parameter range of $T_1$, a full parameter range of D, a full parameter range of $T_1/T_2$, where the full parameter range of $T_1/T_2$ includes fewer bins than the number of $T_1$ bins and D bins. The full parameter range of $T_1/T_2$ can be between about 1 and 10, the full parameter range of $T_1$ can be between about 0.5 seconds and 5 seconds, and the full parameter range of D can be between about $10^{-9}$ cm$^2$/s and $10^{-2}$ cm$^2$/s. The second inversion can be carried out using Eqns. 5 and 10, where $R=T_1/T_2$. The system can further include a display communicatively coupled to the NMR data processing unit, where the display is configured to display the second inversion result as a D–$T_1$ map. The system can further include deriving the $T_1$ distribution and the $T_2$ distribution. The $T_1$ distribution can be determined using Eqn. 12 and the $T_2$ distribution can be determined using Eqn. 13.

The NMR data acquired using the system can include multiple echo trains. The system can further include a drill string and the NMR data acquisition tool can be coupled to the drill string or integrated into a bottom-hole assembly near a drill bit on the drill string. The data acquisition memory included in the system can be configured to store the NMR data acquired using the system. The system can further include a transmitter communicatively coupled to the NMR data acquisition processor, where the transmitter is configured to transmit the acquired NMR data to the NMR data processing unit. The system can further include a receiver communicatively coupled to the data processor, where the receiver is configured to receive acquired NMR data from the transmitter. The NMR data processing unit, included in the system, can be located external to the wellbore.

Statements of the Disclosure Include:

Statement 1: An apparatus comprising: a nuclear magnetic resonance (NMR) data acquisition tool; and a NMR data processing unit communicatively coupled to the NMR data acquisition tool; wherein the NMR data acquisition tool comprises: one or more NMR sensors; a NMR data acquisition processor communicatively coupled to the one or more NMR sensors; and data acquisition memory storing instructions that when executed by the data acquisition processor causes the data acquisition processor to acquire NMR data in a time domain from a subterranean formation or core sample therefrom, the NMR data comprising NMR data parameters comprising spin-lattice relaxation ($T_1$), spin-spin relaxation time ($T_2$), and molecular diffusion (D), and wherein each NMR data parameter is comprised in a plurality of bins; and wherein the NMR data processing unit comprises: a data processor; data processing memory storing instructions that when executed by the data processor causes the data processor to: receive the NMR data from the NMR data acquisition; perform a first inversion of the NMR data using a physical constraint in place of $T_1$ to derive D–$T_2$; and perform a second independent inversion of the acquired NMR data using a physical constraint in place of $T_2$ to derive D–$T_1$.

Statement 2: An apparatus according to Statement 1, wherein the physical constraint comprises a finite range of $T_1/T_2$ values for fluids in the bulk state or in rocks.

Statement 3: An apparatus according to Statement 2, wherein the finite range of $T_1/T_2$ values is between about 1 and 10.

Statement 4: An apparatus according to Statement 2 or Statement 3, wherein the first inversion comprises a full parameter range of $T_2$, a full parameter range of D, and a full parameter range of $T_1/T_2$, wherein the full parameter range of $T_1/T_2$ comprises fewer bins than the number of $T_2$ bins and D bins.

Statement 5: An apparatus according to any one of the preceding Statements 2-4, wherein the full parameter range of $T_1/T_2$ is between about 1 and 10, the full parameter range of $T_2$ is between about 0.5 seconds and 5 seconds, and the full parameter range of D is between about $10^{-9}$ cm$^2$/s and $10^{-2}$ cm$^2$/s.

Statement 6: An apparatus according to any one of the preceding Statements 1-5, wherein the first inversion comprises the following series of equations:

$$E(i,j,k)=\sum_{m=1}^{M'}\sum_{n=1}^{N}\sum_{p=1}^{P}E_{0,mnp}[1-\exp(-t_{W_k}/R_m T_{2,n})]\exp(-i\cdot t_E/T_{2,n})\exp(-\gamma^2 G_i^2 i\cdot t_{E_j}^3 D_p/12);$$

$$E_{0,mnp} \geq 0;$$

where $R=T_1/T_2$.

Statement 7: An apparatus according to any one of the preceding Statements 1-6, further comprising a display communicatively coupled to the NMR data processing unit, wherein the display is configured to display the first inversion result as a D–$T_2$ map.

Statement 8: An apparatus according to any one of the preceding Statements 2-7, wherein the second inversion comprises a full parameter range of $T_1$, a full parameter range of D, a full parameter range of $T_1/T_2$, wherein the full parameter range of $T_1/T_2$ comprises fewer bins than the number of $T_1$ bins and D bins.

Statement 9: An apparatus according to any one of the preceding Statements 2-8, wherein the full parameter range of $T_1/T_2$ is between about 1 and 10, the full parameter range of $T_1$ is between about 0.5 seconds and 5 seconds, and the full parameter range of D is between about $10^{-9}$ cm$^2$/s and $10^{-2}$ cm$^2$/s.

Statement 10: An apparatus according to any one of the preceding Statements 1-9, wherein the second inversion comprises the following series of equations:

$$E(i,j,k)=\sum_{m=1}^{M'}\sum_{n=1}^{N}\sum_{p=1}^{P}E_{0,mnp}[1-\exp(-t_{W_k}/T_{1,n})]\exp(-i\cdot t_E R_m/T_{1,n})\exp(-\gamma^2 G_i^2 i\cdot t_{E_j}^3 D_p/12);$$

$$E_{0,mnp} \geq 0;$$

where $R=T_1/T_2$.

Statement 11: An apparatus according to any one of the preceding Statements 1-10, further comprising a display communicatively coupled to the NMR data processing unit, wherein the display is configured to display the second inversion result as a D–$T_1$ map.

Statement 12: An apparatus according to any one of the preceding Statements 1-11, further comprising deriving the $T_1$ distribution and the $T_2$ distribution, wherein deriving the $T_1$ distribution comprises the following equation:

$$\phi_{T1,i} = \sum_{p=1}^{P} E_{0,np}$$

where:
n=1:N $T_1$ bins;
p=1:P R bins; and
wherein deriving the $T_2$ distribution comprises the following equation:

$$\phi_{T2,i} = \sum_{p=1}^{P} E_{0,mp}$$

where:
m=1:M $T_2$ bins; and
p=1:P R bins.

Statement 13: An apparatus according to any one of the preceding Statements 1-12, wherein the NMR data comprises multiple echo trains.

Statement 14: An apparatus according to any one of the preceding Statements 1-13, wherein the NMR data acquisition tool is configured to be coupled to a drill string.

Statement 15: An apparatus according to any one of the preceding Statements 1-14, wherein the NMR data acquisition tool is configured to be integrated into a bottom-hole assembly near a drill bit.

Statement 16: An apparatus according to any one of the preceding Statements 1-15, wherein the data acquisition memory is configured to store the acquired NMR data.

Statement 17: An apparatus according to any one of the preceding Statements 1-16, further comprising a transmitter communicatively coupled to the NMR data acquisition processor, wherein the transmitter is configured to transmit the acquired NMR data to the NMR data processing unit.

Statement 18: An apparatus according to any one of the preceding Statements 1-17, further comprising a receiver communicatively coupled to the data processor, wherein the receiver is configured to receive acquired NMR data from the transmitter.

Statement 19: A method of evaluating a subsurface formation, the method comprising: providing a nuclear magnetic resonance (NMR) data acquisition tool comprising: one or more NMR sensors; a NMR data acquisition processor communicatively coupled to the one or more NMR sensors; and a data acquisition memory communicatively coupled to the NMR data acquisition processor and storing instructions that when executed by the data acquisition processor causes the data acquisition processor to acquire NMR data in a time domain from a subterranean formation; lowering the NMR data acquisition tool to a desired location within a wellbore; acquiring, at the NMR data acquisition tool, NMR data, wherein the NMR data comprises NMR data parameters comprising spin-lattice relaxation ($T_1$), spin-spin relaxation time ($T_2$), and molecular diffusion (D), and wherein each NMR data parameter is comprised in a plurality of bins; receiving the acquired NMR data at a NMR data processing unit communicatively coupled to the NMR data acquisition tool, the NMR data processing unit comprising a data processor and data processing memory; performing, at the data processor, a first inversion of the NMR data using a physical constraint in place of $T_1$ to derive D–$T_2$; and performing, at the data processor, a second independent inversion of the acquired NMR data using a physical constraint in place of $T_2$ to derive D–$T_1$.

Statement 20: A method according to Statement 19, wherein the physical constraint comprises a finite range of $T_1/T_2$ values for fluids in the bulk state or in rocks.

Statement 21: A method according to Statement 20, wherein the finite range of $T_1/T_2$ values is between about 1 and 10.

Statement 22: A method according to Statement 20 or Statement 21, wherein the first inversion comprises a full parameter range of $T_2$, a full parameter range of D, and a full parameter range of $T_1/T_2$, wherein the full parameter range of $T_1/T_2$ comprises fewer bins than the number of $T_2$ bins and D bins.

Statement 23: A method according to any one of the preceding Statements 20-22, wherein the full parameter range of $T_1/T_2$ is between about 1 and 10, the full parameter range of $T_2$ is between about 0.5 seconds and 5 seconds, and the full parameter range of D is between about $10^{-9}$ cm$^2$/s and $10^{-2}$ cm$^2$/s.

Statement 24: A method according to any one of the preceding Statements 19-23, wherein the first inversion comprises the following series of equations:

$$E(i,j,k) = \sum_{m=1}^{M} \sum_{n=1}^{N} \sum_{p=1}^{P} E_{0,mnp}[1-\exp(-t_{W_k}/R_m T_{2,n})]\exp(-i \cdot t_E/T_{2,n})\exp(-\gamma^2 G_i^2 i \cdot t_{E_j}^3 D_p/12);$$

$$E_{0,mnp} \geq 0;$$

where $R = T_1/T_2$.

Statement 25: A method according to any one of the preceding Statements 19-24, further comprising displaying, at the NMR data processing unit, the first inversion result as a D–$T_2$ map.

Statement 26: A method according to any one of the preceding Statements 20-25, wherein the second inversion comprises a full parameter range of $T_1$, a full parameter range of D, a full parameter range of $T_1/T_2$, wherein the full parameter range of $T_1/T_2$ comprises fewer bins than the number of $T_1$ bins and D bins.

Statement 27: A method according to any one of the preceding Statements 20-26, wherein the full parameter range of $T_1/T_2$ is between about 1 and 10, the full parameter range of $T_1$ is between about 0.5 seconds and 5 seconds, and the full parameter range of D is between about $10^{-9}$ cm$^2$/s and $10^{-2}$ cm$^2$/s.

Statement 28: A method according to any one of the preceding Statements 19-27, wherein the second inversion comprises the following series of equations:

$$E(i,j,k) = \sum_{m=1}^{M} \sum_{n=1}^{N} \sum_{p=1}^{P} E_{0,mnp}[1-\exp(-t_{W_k}/T_{1,n})]\exp(-i \cdot t_E R_m/T_{1,n})\exp(-\gamma^2 G_i^2 i \cdot t_{E_j}^3 D_p/12);$$

$$E_{0,mnp} \geq 0;$$

where $R = T_1/T_2$.

Statement 29: A method according to any one of the preceding Statements 19-28, further comprising displaying, at the NMR processing unit, the second inversion result as a D–$T_1$ map.

Statement 30: A method according to any one of the preceding Statements 19-29, further comprising deriving the $T_1$ distribution and the $T_2$ distribution, wherein deriving the $T_1$ distribution comprises the following equation:

$$\phi_{T1,i} = \sum_{p=1}^{P} E_{0,np}$$

where:
n=1:N $T_1$ bins;
p=1:P R bins; and
wherein deriving the $T_2$ distribution comprises the following equation:

$$\phi_{T2,i} = \sum_{p=1}^{P} E_{0,mp}$$

where:

m=1:M $T_2$ bins; and p=1:P R bins.

Statement 31: A method according to any one of the preceding Statements 19-30, wherein the NMR data comprises multiple echo trains.

Statement 32: A method according to any one of the preceding Statements 19-31, wherein the NMR data acquisition tool is coupled to a drill string.

Statement 33: A method according to any one of the preceding Statements 19-32, wherein the NMR data acquisition tool is integrated into a bottom-hole assembly near a drill bit.

Statement 34: A method according to any one of the preceding Statements 19-33, further comprising storing the NMR data at the data acquisition memory.

Statement 35: A method according to any one of the preceding Statements 19-34, further comprising transmitting the NMR data from the NMR data acquisition tool and receiving the NMR data at the NMR data processing unit.

Statement 36: A system for evaluating a subterranean formation or core sample therefrom, the system comprising: an apparatus comprising a nuclear magnetic resonance (NMR) data acquisition tool and a NMR data processing unit communicatively coupled to the NMR data acquisition tool, wherein the NMR data acquisition tool comprises: one or more NMR sensors; a NMR data acquisition processor communicatively coupled to the one or more NMR sensors; and data acquisition memory storing instructions that when executed by the data acquisition processor causes the data acquisition processor to acquire NMR data in a time domain from a subterranean formation or core sample therefrom, the NMR data comprising NMR data parameters comprising spin-lattice relaxation ($T_1$), spin-spin relaxation time ($T_2$), and molecular diffusion (D), and wherein each NMR data parameter is comprised in a plurality of bins; and wherein the NMR data processing unit comprises: a data processor and data processing memory storing instructions that when executed by the data processor causes the data processor to: receive the NMR data from the NMR data acquisition; perform a first inversion of the NMR data using a physical constraint in place of $T_1$ to derive $D-T_2$; and perform a second independent inversion of the acquired NMR data using a physical constraint in place of $T_2$ to derive $D-T_1$.

Statement 37: A system according to Statement 36, wherein the physical constraint comprises a finite range of $T_1/T_2$ values for fluids in the bulk state or in rocks.

Statement 38: A system according to Statement 37, wherein the finite range of $T_1/T_2$ values is between about 1 and 10.

Statement 39: A system according to Statement 37 or Statement 38, wherein the first inversion comprises a full parameter range of $T_2$, a full parameter range of D, and a full parameter range of $T_1/T_2$, wherein the full parameter range of $T_1/T_2$ comprises fewer bins than the number of $T_2$ bins and D bins.

Statement 40: A system according to any one of the preceding Statements 37-39, wherein the full parameter range of $T_1/T_2$ is between about 1 and 10, the full parameter range of $T_2$ is between about 0.5 seconds and 5 seconds, and the full parameter range of D is between about $10^{-9}$ cm$^2$/s and $10^{-2}$ cm$^2$/s.

Statement 41: A system according to any one of the preceding Statements 36-40, wherein the first inversion comprises the following series of equations:

$$E(i,j,k) = \Sigma_{m=1}^{M} \Sigma_{n=1}^{N} \Sigma_{p=1}^{P} E_{0,mnp}[1-\exp(-t_{W_k}/R_m T_{2,n})]\exp(-i \cdot t_E/T_{2,n})\exp(-\gamma^2 G_i^2 i \cdot t_{E_j}^3 D_p/12);$$

$$E_{0,mnp} \geq 0;$$

where $R = T_1/T_2$.

Statement 42: A system according to any one of the preceding Statements 36-41, further comprising a display communicatively coupled to the NMR data processing unit, wherein the display is configured to display the first inversion result as a $D-T_2$ map.

Statement 43: A system according to any one of the preceding Statements 37-42, wherein the second inversion comprises a full parameter range of $T_1$, a full parameter range of D, a full parameter range of $T_1/T_2$, wherein the full parameter range of $T_1/T_2$ comprises fewer bins than the number of $T_1$ bins and D bins.

Statement 44: A system according to any one of the preceding Statements 37-43, wherein the full parameter range of $T_1/T_2$ is between about 1 and 10, the full parameter range of $T_1$ is between about 0.5 seconds and 5 seconds, and the full parameter range of D is between about $10^{-9}$ cm$^2$/s and $10^{-2}$ cm$^2$/s.

Statement 45: A system according to any one of the preceding Statements 36-44, wherein the second inversion comprises the following series of equations:

$$E(i,j,k) = \Sigma_{m=1}^{M} \Sigma_{n=1}^{N} \Sigma_{p=1}^{P} E_{0,mnp}[1-\exp(-t_{W_k}/T_{1,n})]\exp(-i \cdot t_E R_m/T_{1,n})\exp(-\gamma^2 G_i^2 i \cdot t_{E_j}^3 D_p/12);$$

$$E_{0,mnp} \geq 0;$$

where $R = T_1/T_2$.

Statement 46: A system according to any one of the preceding Statements 36-45, further comprising a display communicatively coupled to the NMR data processing unit, wherein the display is configured to display the second inversion result as a $D-T_1$ map.

Statement 47: A system according to any one of the preceding Statements 36-46, further comprising deriving the $T_1$ distribution and the $T_2$ distribution, wherein deriving the $T_1$ distribution comprises the following equation:

$$\phi_{T1,i} = \sum_{p=1}^{P} E_{0,np}$$

where:

n=1:N $T_1$ bins;

p=1:P R bins; and wherein deriving the $T_2$ distribution comprises the following equation:

$$\phi_{T2,i} = \sum_{p=1}^{P} E_{0,mp}$$

where:

m=1:M $T_2$ bins; and p=1:P R bins.

Statement 48: A system according to any one of the preceding Statements 36-47, wherein the NMR data comprises multiple echo trains.

Statement 49: A system according to any one of the preceding Statements 36-48, further comprising a drill string, wherein the NMR data acquisition tool is coupled to the drill string.

Statement 50: A system according to any one of the preceding Statements 36-49, further comprising a drill string, wherein the NMR data acquisition tool is integrated into a bottom-hole assembly near a drill bit on the drill string.

Statement 51: A system according to any one of the preceding Statements 36-50, wherein the data acquisition memory is configured to store the acquired NMR data.

Statement 52: A system according to any one of the preceding Statements 36-51, further comprising a transmitter communicatively coupled to the NMR data acquisition processor, wherein the transmitter is configured to transmit the acquired NMR data to the NMR data processing unit.

Statement 53: A system according to any one of the preceding Statements 36-52, further comprising a receiver communicatively coupled to the data processor, wherein the receiver is configured to receive acquired NMR data from the transmitter.

Statement 54: A system according to any one of the preceding Statements 36-53, wherein the NMR data processing unit is located external to the wellbore.

Statement 55: A system according to any one of the preceding Statements 36-54, further comprising a core sampling tool deployable in a wellbore, configured to obtain one or more core samples from a subterranean formation therein.

Statement 56: A method of evaluating a core sample obtained from a subterranean formation, the method comprising: providing a nuclear magnetic resonance (NMR) data acquisition tool comprising: one or more NMR sensors; a NMR data acquisition processor communicatively coupled to the one or more NMR sensors; and a data acquisition memory communicatively coupled to the NMR data acquisition processor and storing instructions that when executed by the data acquisition processor causes the data acquisition processor to acquire NMR data in a time domain from a core sample obtained from a subterranean formation; lowering a core sampling tool into a wellbore and extracting a core sample from a subterranean formation therein; acquiring, at the NMR data acquisition tool, NMR data, wherein the NMR data comprises NMR data parameters comprising spin-lattice relaxation ($T_1$), spin-spin relaxation time ($T_2$), and molecular diffusion (D), and wherein each NMR data parameter is comprised in a plurality of bins; receiving the acquired NMR data at a NMR data processing unit communicatively coupled to the NMR data acquisition tool, the NMR data processing unit comprising a data processor and data processing memory; performing, at the data processor, a first inversion of the NMR data using a physical constraint in place of $T_1$ to derive $D-T_2$; and performing, at the data processor, a second independent inversion of the acquired NMR data using a physical constraint in place of $T_2$ to derive $D-T_1$.

Statement 57: A method according to Statement 56, wherein the physical constraint comprises a finite range of $T_1/T_2$ values for fluids in the bulk state or in rocks.

Statement 58: A method according to Statement 57, wherein the finite range of $T_1/T_2$ values is between about 1 and 10.

Statement 59: A method according to Statement 57 or Statement 58, wherein the first inversion comprises a full parameter range of $T_2$, a full parameter range of D, and a full parameter range of $T_1/T_2$, wherein the full parameter range of $T_1/T_2$ comprises fewer bins than the number of $T_2$ bins and D bins.

Statement 60: A method according to any one of the preceding Statements 57-59, wherein the full parameter range of $T_1/T_2$ is between about 1 and 10, the full parameter range of $T_2$ is between about 0.5 seconds and 5 seconds, and the full parameter range of D is between about $10^{-9}$ cm$^2$/s and $10^{-2}$ cm$^2$/s.

Statement 61: A method according to any one of the preceding Statements 56-60, wherein the first inversion comprises the following series of equations:

$$E(i,j,k) = \sum_{m=1}^{M}\sum_{n=1}^{N}\sum_{p=1}^{P} E_{0,mnp}[1-\exp(-t_{W_k}/R_m T_{2,n})]\exp(-i \cdot t_E/T_{2,n})\exp(-\gamma^2 G_i^2 \cdot t_{E_j}^3 D_p/12);$$

$$E_{0,mnp} \geq 0;$$

where $R = T_1/T_2$.

Statement 62: A method according to any one of the preceding Statements 56-61, further comprising displaying, at the NMR data processing unit, the first inversion result as a $D-T_2$ map.

Statement 63: A method according to any one of the preceding Statements 57-62, wherein the second inversion comprises a full parameter range of $T_1$, a full parameter range of D, a full parameter range of $T_1/T_2$, wherein the full parameter range of $T_1/T_2$ comprises fewer bins than the number of $T_1$ bins and D bins.

Statement 64: A method according to any one of the preceding Statements 57-63, wherein the full parameter range of $T_1/T_2$ is between about 1 and 10, the full parameter range of $T_1$ is between about 0.5 seconds and 5 seconds, and the full parameter range of D is between about $10^{-9}$ cm$^2$/s and $10^{-2}$ cm$^2$/s.

Statement 65: A method according to any one of the preceding Statements 56-64, wherein the second inversion comprises the following series of equations:

$$E(i,j,k) = \sum_{m=1}^{M}\sum_{n=1}^{N}\sum_{p=1}^{P} E_{0,mnp}[1-\exp(-t_{W_k}/T_{1,n})]\exp(-i \cdot t_E R_m/T_{1,n})\exp(-\gamma^2 G_i^2 \cdot t_{E_j}^3 D_p/12);$$

$$E_{0,mnp} \geq 0;$$

where $R = T_1/T_2$.

Statement 66: A method according to any one of the preceding Statements 56-65, further comprising displaying, at the NMR processing unit, the second inversion result as a $D-T_1$ map.

Statement 67: A method according to any one of the preceding Statements 56-66, further comprising deriving the $T_1$ distribution and the $T_2$ distribution, wherein deriving the $T_1$ distribution comprises the following equation:

$$\phi_{T1,i} = \sum_{p=1}^{P} E_{0,np}$$

where:
n=1:N $T_1$ bins;
p=1:P R bins; and
wherein deriving the $T_2$ distribution comprises the following equation:

$$\phi_{T2,i} = \sum_{p=1}^{P} E_{0,mp}$$

where:

m=1:M $T_2$ bins; and p=1:P R bins.

Statement 68: A method according to any one of the preceding Statements 56-67, wherein the NMR data comprises multiple echo trains.

Statement 69: A method according to any one of the preceding Statements 56-68, further comprising storing the NMR data at the data acquisition memory.

Statement 70: A method according to any one of the preceding Statements 56-69, further comprising transmitting the NMR data from the NMR data acquisition tool and receiving the NMR data at the NMR data processing unit.

Statement 71: A method according to any one of the preceding Statement 56-70, further comprising retrieving the core sample from the wellbore.

Statement 72: A method of independently deriving D–$T_1$ and D–$T_2$ from the same set of acquired NMR data, the method comprising: receiving NMR data in a time domain acquired from a subterranean formation or core sample therefrom, wherein the NMR data comprises NMR data parameters comprising spin-lattice relaxation ($T_1$), spin-spin relaxation time ($T_2$), and molecular diffusion (D), and wherein each NMR data parameter is comprised in a plurality of bins; performing a first inversion of the NMR data using a physical constraint in place $T_1$ to derive D–$T_2$; and performing a second independent inversion of the acquired NMR data using a physical constraint in place of $T_2$ to derive D–$T_1$.

Statement 73: A method according to Statement 72, wherein the physical constraint comprises a finite range of $T_1/T_2$ values for fluids in the bulk state or in rocks.

Statement 74: A method according to Statement 73, wherein the finite range of $T_1/T_2$ values is between about 1 and 10.

Statement 75: A method according to Statement 73 or Statement 74, wherein the first inversion comprises a full parameter range of $T_2$, a full parameter range of D, and a full parameter range of $T_1/T_2$, wherein the full parameter range of $T_1/T_2$ comprises fewer bins than the number of $T_2$ bins and D bins.

Statement 76: A method according to any one of the preceding Statements 73-75, wherein the full parameter range of $T_1/T_2$ is between about 1 and 10, the full parameter range of $T_2$ is between about 0.5 seconds and 5 seconds, and the full parameter range of D is between about $10^{-9}$ cm$^2$/s and $10^{-2}$ cm$^2$/s.

Statement 77: A method according to any one of the preceding Statements 72-76, wherein the first inversion comprises the following series of equations:

$$E(i,j,k) = \Sigma_{m=1}^{M} \Sigma_{n=1}^{N} \Sigma_{p=1}^{P} E_{0,mnp}[1-\exp(-t_{W_k}/R_m T_{2,n})] \exp(-i \cdot t_E/T_{2,n}) \exp(-\gamma^2 G_i^2 i \cdot t_{E_j}^3 D_p/12);$$

$$E_{0,mnp} \geq 0;$$

where R=$T_1/T_2$.

Statement 78: A method according to any one of the preceding Statements 72-77, further comprising displaying, at the NMR data processing unit, the first inversion result as a D–$T_2$ map.

Statement 79: A method according to any one of the preceding Statements 73-78, wherein the second inversion comprises a full parameter range of $T_1$, a full parameter range of D, a full parameter range of $T_1/T_2$, wherein the full parameter range of $T_1/T_2$ comprises fewer bins than the number of $T_1$ bins and D bins.

Statement 80: A method according to any one of the preceding Statements 73-79, wherein the full parameter range of $T_1/T_2$ is between about 1 and 10, the full parameter range of $T_1$ is between about 0.5 seconds and 5 seconds, and the full parameter range of D is between about $10^{-9}$ cm$^2$/s and $10^{-2}$ cm$^2$/s.

Statement 81: A method according to any one of the preceding Statements 72-80, wherein the second inversion comprises the following series of equations:

$$E(i,j,k) = \Sigma_{m=1}^{M} \Sigma_{n=1}^{N} \Sigma_{p=1}^{P} E_{0,mnp}[1-\exp(-t_{W_k}/T_{1,n})] \exp(-i \cdot t_E/T_{1,n}) \exp(-\gamma^2 G_i^2 i \cdot t_{E_j}^3 D_p/12);$$

$$E_{0,mnp} \geq 0;$$

where R=$T_1/T_2$.

Statement 82: A method according to any one of the preceding Statements 72-81, further comprising displaying, at the NMR processing unit, the second inversion result as a D–$T_1$ map.

Statement 83: A method according to any one of the preceding Statements 72-82, further comprising deriving the $T_1$ distribution and the $T_2$ distribution, wherein deriving the $T_1$ distribution comprises the following equation:

$$\phi_{T1,i} = \sum_{p=1}^{P} E_{0,np}$$

where:

n=1:N $T_1$ bins;

p=1:P R bins; and wherein deriving the $T_2$ distribution comprises the following equation:

$$\phi_{T2,i} = \sum_{p=1}^{P} E_{0,mp}$$

where:

m=1:M $T_2$ bins; and p=1:P R bins.

Statement 84: A method according to any one of the preceding Statements 72-83, wherein the NMR data comprises multiple echo trains.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Moreover, claim language reciting "at least one of" a set indicates that a system including either one member of the set, or multiple members of the set, or all members of the set, satisfies the claim.

We claim:

1. An apparatus comprising:
a nuclear magnetic resonance (NMR) data acquisition tool; and
a NMR data processing unit communicatively coupled to the NMR data acquisition tool;
wherein the NMR data acquisition tool comprises:
one or more NMR sensors;
a NMR data acquisition processor communicatively coupled to the one or more NMR sensors; and
data acquisition memory storing instructions that when executed by the data acquisition processor causes the data acquisition processor to acquire NMR data in a time domain from a subterranean formation or core sample therefrom, the NMR data comprising NMR data parameters comprising spin-lattice relaxation time ($T_1$), spin-spin relaxation time ($T_2$), and molecular diffusion (D), and wherein each NMR data parameter is comprised in a plurality of bins; and
wherein the NMR data processing unit comprises:
a data processor;
data processing memory storing instructions that when executed by the data processor causes the data processor to:
receive the NMR data from the NMR data acquisition;
perform a first inversion of the NMR data using a physical constraint in place of $T_1$ to derive $D-T_2$; and
perform a second independent inversion of the acquired NMR data using a physical constraint in place of $T_2$ to derive $D-T_1$.

2. The apparatus of claim 1, further comprising a display communicatively coupled to the NMR data processing unit, wherein the display is configured to display the first inversion result as a $D-T_2$ map and the second inversion result as a $D-T_1$ map.

3. The apparatus of claim 2, further comprising:
a transmitter communicatively coupled to the NMR data acquisition processor, wherein the transmitter is configured to transmit the acquired NMR data to the NMR data processing unit; and
a receiver communicatively coupled to the data processor, wherein the receiver is configured to receive acquired NMR data from the transmitter.

4. The apparatus of claim 1, wherein the NMR data acquisition tool is configured to be coupled to a drill string.

5. A method of evaluating a subsurface formation, the method comprising:
providing a nuclear magnetic resonance (NMR) data acquisition tool comprising:
one or more NMR sensors;
a NMR data acquisition processor communicatively coupled to the one or more NMR sensors; and
a data acquisition memory communicatively coupled to the NMR data acquisition processor and storing instructions that when executed by the data acquisition processor causes the data acquisition processor to acquire NMR data in a time domain from a subterranean formation;
lowering the NMR data acquisition tool to a desired location within a wellbore;
acquiring, at the NMR data acquisition tool, NMR data, wherein the NMR data comprises NMR data parameters comprising spin-lattice relaxation time ($T_1$), spin-spin relaxation time ($T_2$), and molecular diffusion (D), and wherein each NMR data parameter is comprised in a plurality of bins;
receiving the acquired NMR data at a NMR data processing unit communicatively coupled to the NMR data acquisition tool, the NMR data processing unit comprising a data processor and data processing memory;
performing, at the data processor, a first inversion of the NMR data using a physical constraint in place of $T_1$ to derive $D-T_2$; and
performing, at the data processor, a second independent inversion of the acquired NMR data using a physical constraint in place of $T_2$ to derive $D-T_1$.

6. The method of claim 5, wherein the physical constraint comprises a finite range of $T_1/T_2$ values for fluids in the bulk state or in rocks.

7. The method of claim 6, wherein the finite range of $T_1/T_2$ values is between about 1 and 10.

8. The method of claim 7, wherein the first inversion comprises a full parameter range of $T_2$, a full parameter range of D, and a full parameter range of $T_1/T_2$, wherein the full parameter range of $T_1/T_2$ comprises fewer bins than the number of $T_2$ bins and D bins.

9. The method of claim 8, wherein the full parameter range of $T_1/T_2$ is between about 1 and 10, the full parameter range of $T_2$ is between about 0.5 seconds and 5 seconds, and the full parameter range of D is between about $10^{-9}$ cm²/s and $10^{-2}$ cm²/s.

10. The method of claim 9, wherein the first inversion comprises the following series of equations:

$$E(i,j,k)=\Sigma_{m=1}^{M'}\Sigma_{n=1}^{N}\Sigma_{p=1}^{P}E_{0,mnp}[1-\exp(-t_{W_k}/R_m T_{2,n})]\exp(-i\cdot t_E/T_{2,n})\exp(-\gamma^2 G_i^2 i\cdot t_{E_j}^3 D_p/12);$$

$$E_{0,mnp} \geq 0;$$

where $R=T_1/T_2$.

11. The method of claim 9, further comprising displaying, at the NMR data processing unit, the first inversion result as a $D-T_2$ map.

12. The method of claim 7, wherein the second inversion comprises a full parameter range of $T_1$, a full parameter range of D, a full parameter range of $T_1/T_2$, wherein the full parameter range of $T_1/T_2$ comprises fewer bins than the number of $T_1$ bins and D bins.

13. The method of claim 12, wherein the full parameter range of $T_1/T_2$ is between about 1 and 10, the full parameter range of $T_1$ is between about 0.5 seconds and 5 seconds, and the full parameter range of D is between about $10^{-9}$ cm²/s and $10^{-2}$ cm²/s.

14. The method of claim 13, wherein the second inversion comprises the following series of equations:

$$E(i,j,k)=\Sigma_{m=1}^{M'}\Sigma_{n=1}^{N}\Sigma_{p=1}^{P}E_{0,mnp}[1-\exp(-t_{W_k}/R_m T_{2,n})]\exp(-i\cdot t_E/T_{2,n})\exp(-\gamma^2 G_i^2 i\cdot t_{E_j}^3 D_p/12);$$

$$E_{0,mnp} \geq 0;$$

where $R=T_1/T_2$.

15. The method of claim 14, further comprising displaying, at the NMR processing unit, the second inversion result as a $D-T_1$ map.

16. The method of claim 5, further comprising deriving a $T_1$ distribution and a $T_2$ distribution, wherein deriving the $T_1$ distribution comprises the following equation:

$$\phi_{T1,i} = \sum_{p=1}^{P} E_{0,np}$$

where:
 n=1:N $T_1$ bins;
 p=1:P R bins; and
wherein deriving the $T_2$ distribution comprises the following equation:

$$\phi_{T2,i} = \sum_{p=1}^{P} E_{0,mp}$$

where:
 m=1:M $T_2$ bins; and
 p=1:P R bins.

17. The method of claim 13, further comprising transmitting the NMR data from the NMR data acquisition tool and receiving the NMR data at the NMR data processing unit.

18. A system for evaluating a subterranean formation or core sample therefrom, the system comprising:
 a nuclear magnetic resonance (NMR) data acquisition tool comprising:
  one or more NMR sensors;
  a NMR data acquisition processor communicatively coupled to the one or more NMR sensors; and
  data acquisition memory storing instructions that when executed by the data acquisition processor causes the data acquisition processor to acquire NMR data in a time domain from a subterranean formation or core sample therefrom, the NMR data comprising NMR data parameters comprising spin-lattice relaxation time ($T_1$), spin-spin relaxation time ($T_2$), and molecular diffusion (D), and wherein each NMR data parameter is comprised in a plurality of bins; and
 a NMR data processing unit communicatively coupled to the NMR data acquisition tool, the NMR data processing unit comprising:
  a data processor and data processing memory storing instructions that when executed by the data processor causes the data processor to:
   receive the NMR data from the NMR data acquisition;
   perform a first inversion of the NMR data using a physical constraint in place of $T_1$ to derive $D-T_2$; and
   perform a second independent inversion of the acquired NMR data using a physical constraint in place of $T_2$ to derive $D-T_1$.

19. The system of claim 18, further comprising a drill string, wherein the NMR data acquisition tool is coupled to the drill string.

20. The system of claim 18, wherein the NMR data processing unit is located external to the wellbore.

* * * * *